US007279695B2

(12) United States Patent
Oguri

(10) Patent No.: US 7,279,695 B2
(45) Date of Patent: Oct. 9, 2007

(54) EDGE POSITION DETECTING APPARATUS AND METHOD, AND PROGRAM

(75) Inventor: Hirofumi Oguri, Nagoya (JP)

(73) Assignee: Brother Kogyo Kabushiki Kaisha, Nagoya-shi, Aichi-ken (JP)

( * ) Notice: Subject to any disclaimer, the term of this patent is extended or adjusted under 35 U.S.C. 154(b) by 48 days.

(21) Appl. No.: 11/189,037

(22) Filed: Jul. 26, 2005

(65) Prior Publication Data

US 2006/0022155 A1    Feb. 2, 2006

(30) Foreign Application Priority Data

Jul. 27, 2004    (JP)    ............................ 2004-219051

(51) Int. Cl.
*G01N 21/86* (2006.01)
(52) U.S. Cl. ............................ 250/559.36; 250/559.24; 101/484; 101/485; 347/19
(58) Field of Classification Search ............ 250/559.24, 250/559.36; 101/484–485; 347/19; 400/708
See application file for complete search history.

(56) References Cited

U.S. PATENT DOCUMENTS

| 4,983,854 | A | * | 1/1991 | Mizuno et al. | ........ 250/559.15 |
| 5,870,114 | A | | 2/1999 | Numata et al. | |
| 6,348,697 | B1 | * | 2/2002 | Kitajima | .................. 250/559.4 |
| 6,622,625 | B1 | * | 9/2003 | Sugiyama | .................... 101/484 |
| 6,966,713 | B2 | * | 11/2005 | Kim | ............................ 400/76 |

FOREIGN PATENT DOCUMENTS

| JP | 3007371 | 1/1991 |
| JP | 5330696 | 12/1993 |

* cited by examiner

*Primary Examiner*—Thanh X. Luu
*Assistant Examiner*—Stephen Yam
(74) *Attorney, Agent, or Firm*—Banner & Witcoff, Ltd

(57) ABSTRACT

There is provided an edge position detecting apparatus that includes a reflective optical sensor that outputs light to a supporting surface of a supporting member, and receives a reflected light; a moving unit that moves the reflective optical sensor; a reflected light data generating unit that generates reflected light data by obtaining a light-receiving signal; and a detecting unit that detects an edge position of the target detection object. The reflected light data generating unit generates the reflected light data when the target detection object is/is not supported by the supporting member. The detecting unit detects the edge position based on a relative change between a first and a second reflected light data. The first reflected light data is generated when the target detection object is supported by the supporting member. The second reflected light data is generated when the target detection object is not supported by the supporting member.

18 Claims, 11 Drawing Sheets

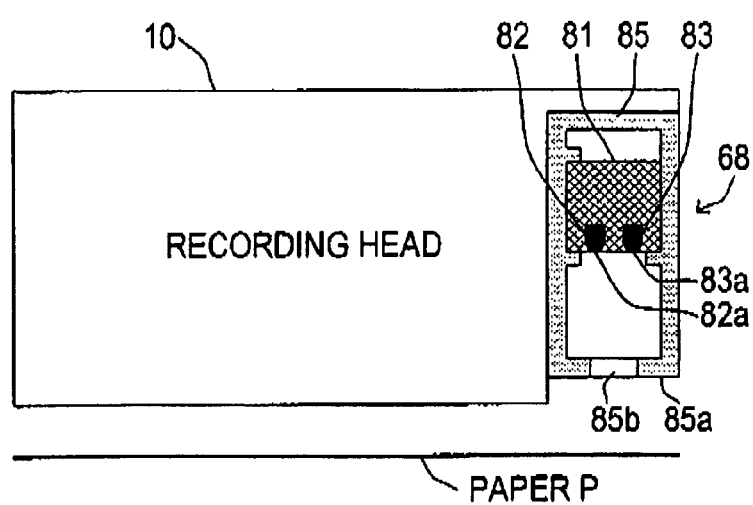
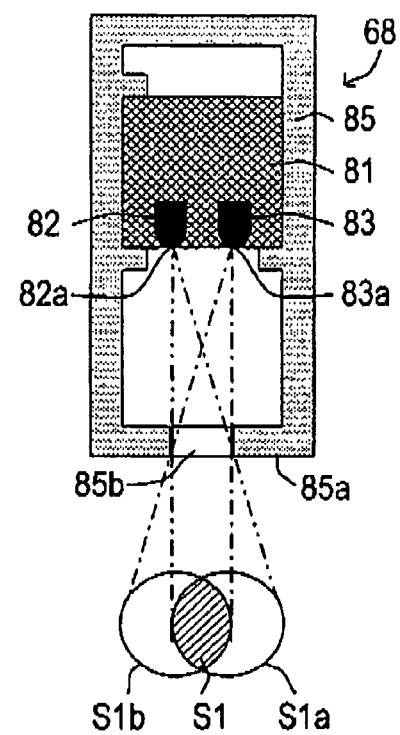

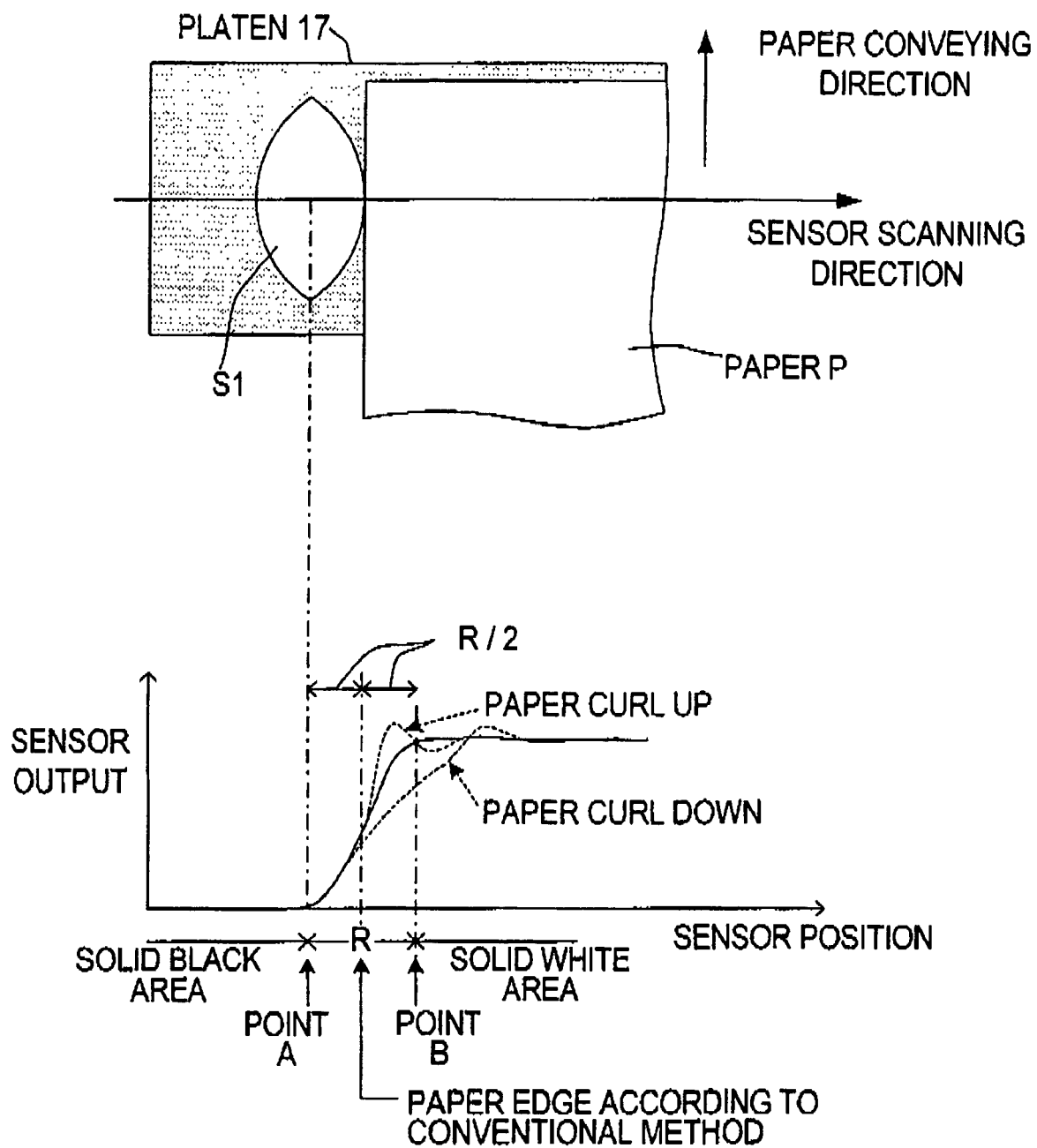

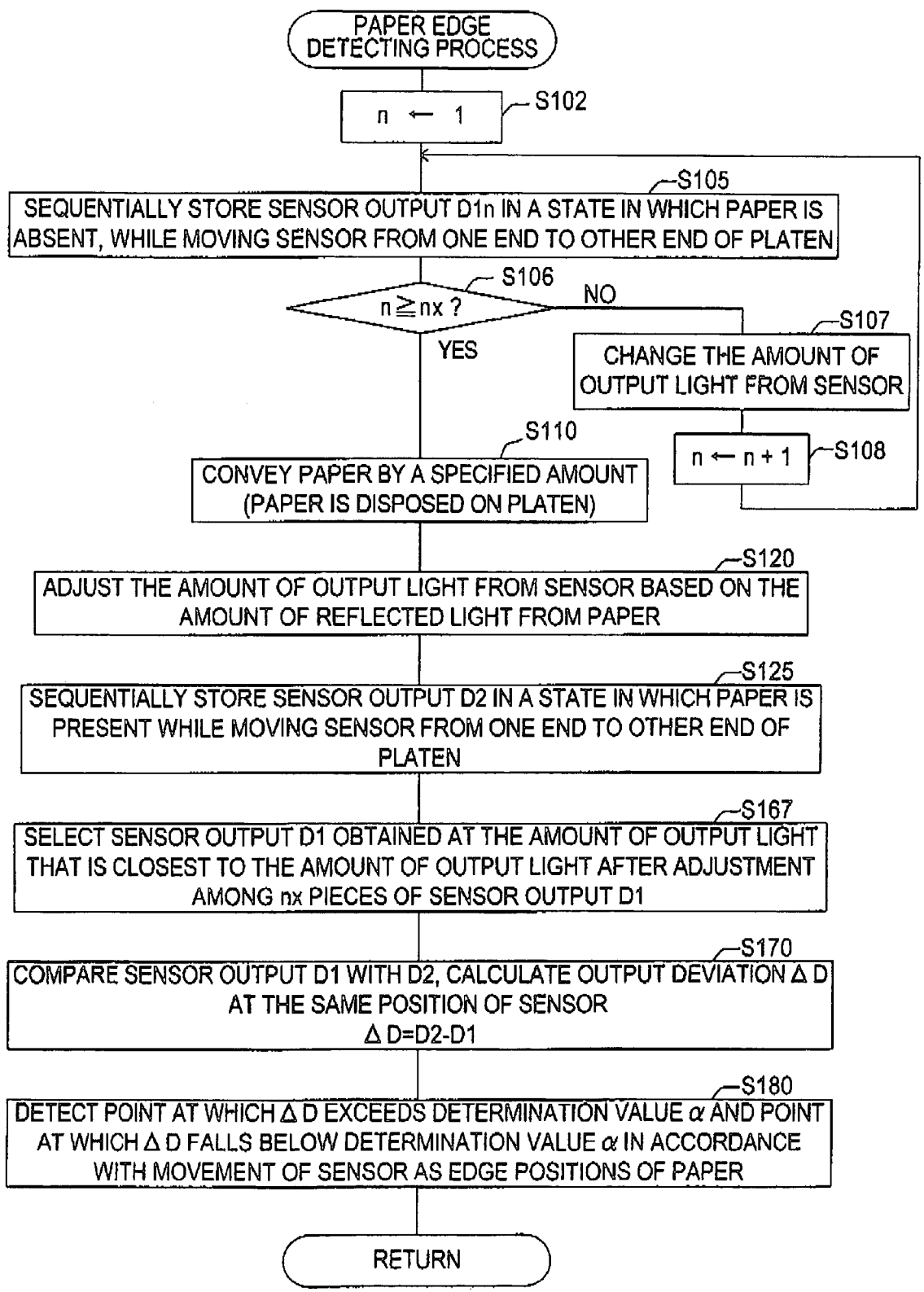

EDGE POSITION DETECTING APPARATUS
AND METHOD, AND PROGRAM

CROSS-REFERENCE TO RELATED APPLICATIONS

This application claims the benefit of Japanese Patent Application NO. 2004-219051 filed Jul. 27, 2004 in the Japanese Patent Office, the disclosure of which is incorporated herein by reference.

BACKGROUND

The present invention relates to an edge position detecting apparatus and method that optically detects an edge position of a target detection object using a reflective optical sensor for transmitting/receiving light, and a program that realizes a part of the functions of the apparatus by means of a computer.

There has been conventionally an image forming apparatus for forming an image on a recording paper via a recording head by moving a carriage provided with the recording head in a main scanning direction perpendicular to a conveying direction of the recording paper. For the image forming apparatus, there has been conventionally known an edge position detecting apparatus that optically detects both edges of the recording paper. In the edge position detecting apparatus, a reflective optical sensor, which is incorporated into the carriage, is moved with the carriage in the main scanning direction. When the reflective optical sensor is moved, the change in the level of a light-receiving signal obtained by the reflective optical sensor is detected, and thereby both edge positions of the recording paper are optically detected.

In such an edge position detecting apparatus, if the recording paper is soiled, the soil changes the signal level of the light-receiving signal obtained by the reflective optical sensor, and consequently the edge positions of the recording paper may be erroneously detected. Therefore, there has also been proposed an edge position detecting apparatus (for example, see Published Publication of Unexamined Japanese Patent Application No. 3-7371). In the apparatus, while the carriage is moved along the recording paper, the light amount of the reflected light received by the reflective optical sensor is detected. The position where the light amount is firstly increased and the position where the light amount is finally decreased are detected as both of the edge positions of the recording paper.

SUMMARY

According to the above proposed apparatus, even if the recording paper, as a target detection object, is more or less soiled, both edge positions of the recording paper can be detected. However, if there is an irregularity in color (white) or concavity and convexity on the surface of the recording paper, or if the edge of the recording paper is curled up/down, the difference between the intensity of reflected light, which is obtained from a portion of the recording paper near the edge position of the recording paper, and the intensity of reflected light, which is obtained from a supporting member (platen, etc) used to support the recording paper, is decreased. Thus, there is a problem in that the edge positions of the recording paper may not be accurately detected.

In view of the foregoing, it is an object of the present invention to provide an edge position detecting apparatus that can accurately detect the edge position of the target detection object without being affected by irregularity in color, concavity and convexity on the surface of the target detection object, and by the curl-up/down of the edge of the target detection object.

In order to attain the above and other objects, the present invention provides an edge position detecting apparatus that includes a reflective optical sensor that outputs light to a supporting surface of a supporting member used to support a target detection object, and that receives a reflected light; a moving unit that moves the reflective optical sensor along the supporting surface of the supporting member in a specified direction; a reflected light data generating unit that generates reflected light data when one of the supporting member and the target detection object on the supporting member is optically scanned in the specified direction by obtaining a light-receiving signal from the reflective optical sensor while moving the reflective optical sensor via the moving unit in the specified direction; and a detecting unit that detects an edge position of the target detection object in the specified direction based on the reflected light data generated by the reflected light data generating unit. The reflected light data generating unit may generate the reflected light data respectively when the target detection object is supported by the supporting member and when the target detection object is not supported by the supporting member. The detecting unit may detect the edge position based on a relative change between a first reflected light data and a second reflected light data. The first reflected light data may be generated by the reflected light data generating unit when the target detection object is supported by the supporting member. The second reflected light data may be generated by the reflected light data generating unit when the target detection object is not supported by the supporting member.

In another aspect of the present invention, there is provided a program that is able to function as a reflected light data generating unit and a detecting unit in the above edge position detecting apparatus by means of a computer.

The program, which comprises an ordered sequence of instructions suitable for processing by a computer, may be provided to a computer or a user who uses the computer through a recording medium such as an FD, a CD-ROM and a memory card, or a communication line network such as the Internet. When provided to a user, the program may be pre-installed in a hard disk or a memory of the computer. The computer to execute the program may be a computer installed in an edge position detecting apparatus, or may be a separate computer capable of data communication with the edge position detecting apparatus.

BRIEF DESCRIPTION OF THE DRAWINGS

The present invention will now be described, by way of example, with reference to the accompanying drawings, in which:

FIG. 1 is a perspective view showing a multifunction device having a printer function, a copier function, a scanner function, a facsimile function, a telephone function, and the like;

FIGS. 3A and 3B are explanatory diagrams showing the cross-sectional construction of a media sensor attached to a carriage (recording head) and a target detection area of the media sensor;

FIG. 8 is an explanatory diagram showing a conventional paper edge detection technique and the associated problems;

FIG. 11 is a flowchart showing another example of the paper edge detecting process in which the paper edge detection is performed without conveying paper in opposing directions.

DETAILED DESCRIPTION OF THE PREFERRED EMBODIMENT

In the preferred embodiment, the present invention is applied to a multifunction device having a printer function, a copier function, a scanner function, a facsimile function, a telephone function, and the like.

Figure 1:
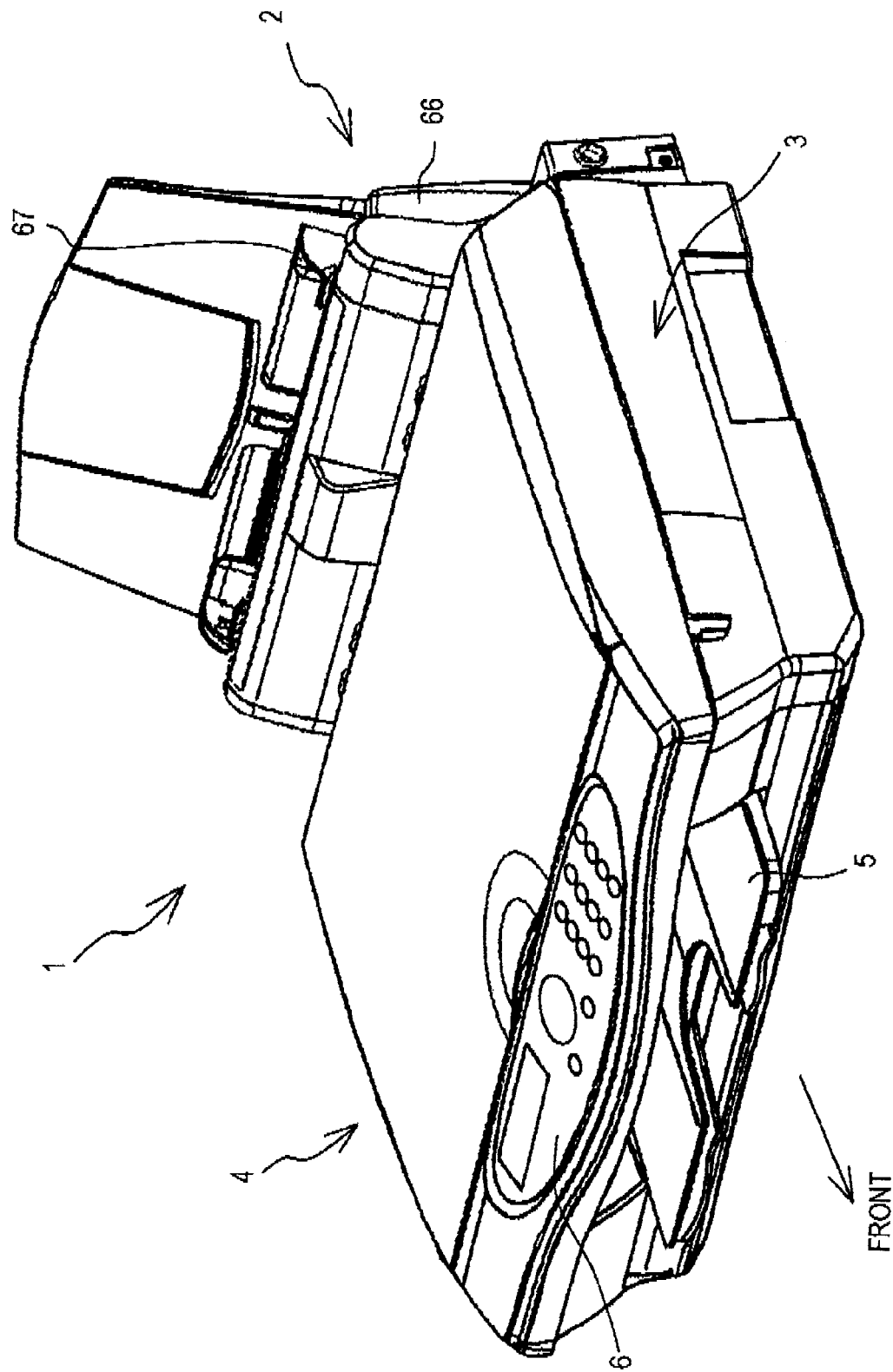

FIG. 1 is a perspective view of a multifunction device 1 of a first embodiment of the present invention.

As shown in FIG. 1, a paper supplying unit 2 is provided in the rear section of the multifunction device 1. An inkjet printer 3 is provided in front of and below the paper supplying unit 2. A scanning unit 4 for implementing the copier function and the facsimile function is provided on the printer 3. A paper discharge tray 5 is provided on the front side of the printer 3. An operation panel 6 is provided on the top surface on the front end of the scanning device 4.

The paper supplying unit 2 includes an inclined wall section 66 and an extended paper guide plate 67, and stacks a plurality of sheets of paper. The inclined wall section 66 accommodates paper in an inclined manner. The extended paper guide plate 67 is detachably attached to the inclined wall section 66. The inclined wall section 66 incorporates a paper feed motor 65 (not shown in FIG. 1. See FIG. 4) and a paper feed roller (not shown). The paper feed roller, which is rotated by the driving force of the paper feed motor 65, conveys paper to the printer 3.

Figure 2:
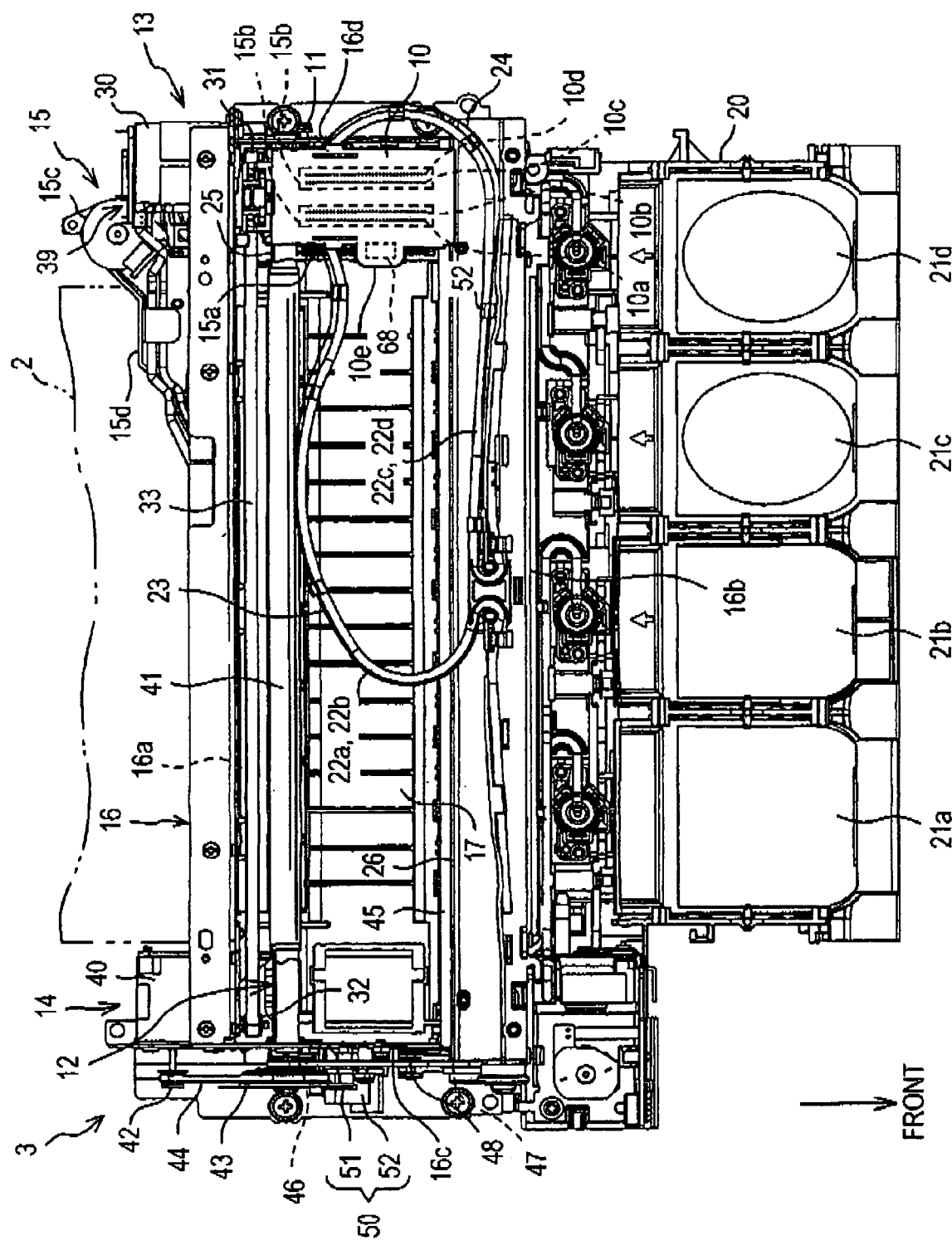
FIG. 2 is a plan view showing the internal construction of a printer provided in the multifunction device.

The printer 3 will be described hereinafter. FIG. 2 is a plan view of the internal configuration of the printer 3.

As shown in FIG. 2, the printer 3 includes a recording head 10, a carriage 11, a guide mechanism 12, a carriage moving mechanism 13, a paper conveying mechanism 14, and a maintenance mechanism 15 for the recording head 10. The recording head 10 is mounted on the carriage 11. The guide mechanism 12 supports the carriage 11 so that the carriage 11 can move reciprocally in the left-to-right direction as a scanning direction. The carriage moving mechanism 13 moves the carriage 11 in the left-to-right direction. The paper conveying mechanism 14 conveys paper supplied by the paper supplying unit 2.

A rectangular frame 16 that is long in the left-to-right direction and that is short in the up-and-down direction is provided in the printer 3. The guide mechanism 12, the carriage moving mechanism 13, the paper conveying mechanism 14, and the maintenance mechanism 15, or the like, are mounted on the frame 16. Furthermore, the recording head 10 and the carriage 11 are accommodated inside the frame 16 so as to be movable in the left-to-right direction.

The frame 16 includes a rear plate 16a and a front plate 16b. A paper introducing opening and a paper discharging opening (not shown) are respectively formed in the rear plate 16a and the front plate 16b. Paper supplied by the paper supplying unit 2 is introduced into the frame 16 via the paper introducing opening, conveyed to the front of the frame 16 by the paper conveying mechanism 14, and discharged through the paper discharging opening onto the paper discharge tray 5 (see FIG. 1) on the front of the multifunction device 1. A black platen 17 having a plurality of ribs is mounted on the bottom surface of the frame 16. The recording head 10 performs recording (image forming) on paper inside the frame 16 as the paper moves over the black platen 17.

The recording head 10 is provided with four sets of ink nozzles 10a-10d that point downward. Paper is printed on by ejecting four colors (black, cyan, yellow, and magenta) of ink through these sets of ink nozzles 10a-10d. Since the four sets of ink nozzles 10a-10d are disposed on the bottom side of the recording head 10, their positions are represented by broken lines in FIG. 2.

Ink cartridges 21a-21d for each of the four colors are mounted in a cartridge holder 20 on the front side of the frame 16. The ink cartridges 21a-21d are connected to the recording head 10 via four flexible ink tubes 22a-22d that pass through the frame 16 in order to supply ink of each of the four colors to the recording head 10.

Left and right FPC (flexible printed circuit) 23 and 24 are disposed inside the frame 16. The left EPC 23 extends together with the ink tubes 22a and 22b and connects to the recording head 10. The right FPC 24 extends together with the ink tubes 22c and 22d and connects to the recording head 10. The FPC 23 and FPC 24 include a plurality of signal lines that electrically connect the recording head 10 to a control process unit 70 (not shown in FIG. 2) described later.

The guide mechanism 12 has a guide shaft 25 and a guide rail 26. The guide shaft 25 extends in the left-to-right direction in the back part of the frame 16. The left and right ends of the guide shaft 25 are respectively coupled with a left plate 16c and a right plate 16d of the frame 16. The guide rail 26 extends in the left-to-right direction in the front part of the frame. The rear end of the carriage 11 is fitted over the guide shaft 25 so as to be capable of sliding along the guide shaft 25, while the front end of the carriage 11 is engaged with the guide rail 26 and is capable of sliding along the guide rail 26.

The carriage moving mechanism 13 includes a carriage motor 30, a drive pulley 31, a follow pulley 32, and a belt 33. The carriage motor 30 is mounted on the frame 16 at the rear side of the rear plate 16a on the right end and facing front. The drive pulley 31 is driven to rotate by the carriage motor 30. The follow pulley 32 is rotatably supported on the left end of the rear plate 16a. The belt 33 is looped around the pulleys 31 and 32 and fixed to the carriage 11. A carriage conveyance encoder 39 is disposed on the carriage motor 30 for detecting a moving amount (moving position) of the carriage 11 (recording head 10).

The paper conveying mechanism 14 includes a paper conveying motor 40, a registration roller 41, a drive pulley 42, a follow pulley 43, and a belt 44. The paper conveying motor 40 is mounted facing leftward on the portion of the left plate 16c that protrudes further rearward than the rear plate 16a. The registration roller 41 extends left-to-right direction in the frame 16 below the guide shaft 25, The left and right ends of the registration roller 41 are rotatably supported in the left plate 16c and right plate 16d, respectively. The drive pulley 42 is driven to rotate by the paper conveying motor 40. The follow pulley 43 is coupled to the left end of the registration roller 41. The belt 44 is looped around the pulleys 42 and 43. When the paper conveying motor 40 is driven, the registration roller 41 rotates and conveys paper in the rear-to-front direction. While the registration roller 41 is emphasized in FIG. 2, the registration roller 41 is actually disposed beneath the guide shaft 25.

The paper conveying mechanism 14 further includes a discharge roller 45, a follow pulley 46, a follow pulley 47, and a belt 48. The discharge roller 45 extends in the left-to-right direction in the front section of the frame 16. The left and right ends of the discharge roller 45 are respectively rotatably supported in the left plate 16c and right plate 16d. The follow pulley 46 is integrally provided with the follow pulley 43. The follow pulley 47 is coupled to the left end of the discharge roller 45. The belt 48 is looped around the pulleys 46 and 47. When the paper conveying motor 40 is driven, the discharge roller 45 rotates and discharges paper toward the paper discharge tray 5 in the front of the multifunction device 1.

An encoder disk 61 is fixed to the follow pulley 43. A photo interrupter 52 having a light-emitting unit and a light-receiving unit is mounted on the left plate 16c so that the encoder disk 51 is interposed between the light-emitting unit and light-receiving unit. The encoder disk 51 and the photo interrupter 52 constitute a paper conveying encoder 50. The control process unit 70 described later controls the driving of the paper conveying motor 40 based on the detection signals from the paper conveying encoder 50 (more specifically, the photo interrupter 52).

The maintenance mechanism 15 includes a wiper 15a, two caps 15b, and a drive motor 15c. The wiper 15a wipes the head surface of the recording head 10. Each of the caps 15b can hermetically seal the two sets of four ink nozzles 10a-10d. The drive motor 15c drives both the wiper 15a and caps 15b. The wiper 15a, caps 15b, and drive motor 15c are mounted on a mounting plate 15d. The mounting plate 15d is fixed to the lower surface side of the bottom plate of the frame 16 at the right portion. Since the caps 15b are disposed on the bottom side of the recording head 10, their positions are represented by broken lines in FIG. 2.

As shown in FIG. 2, a media sensor 68 is mounted on the left end of the recording head 10 for detecting the leading edge, trailing edge, and side edges of paper. The media sensor 68 is a reflective optical sensor that includes a light-emitting unit (light-emitting element) and a light-receiving unit (light-receiving element). The media sensor 68 is mounted on a sensor mounting unit 10e and is facing downward. The sensor mounting unit 10e protrudes from the left side of the recording head 10.

Figure 4:
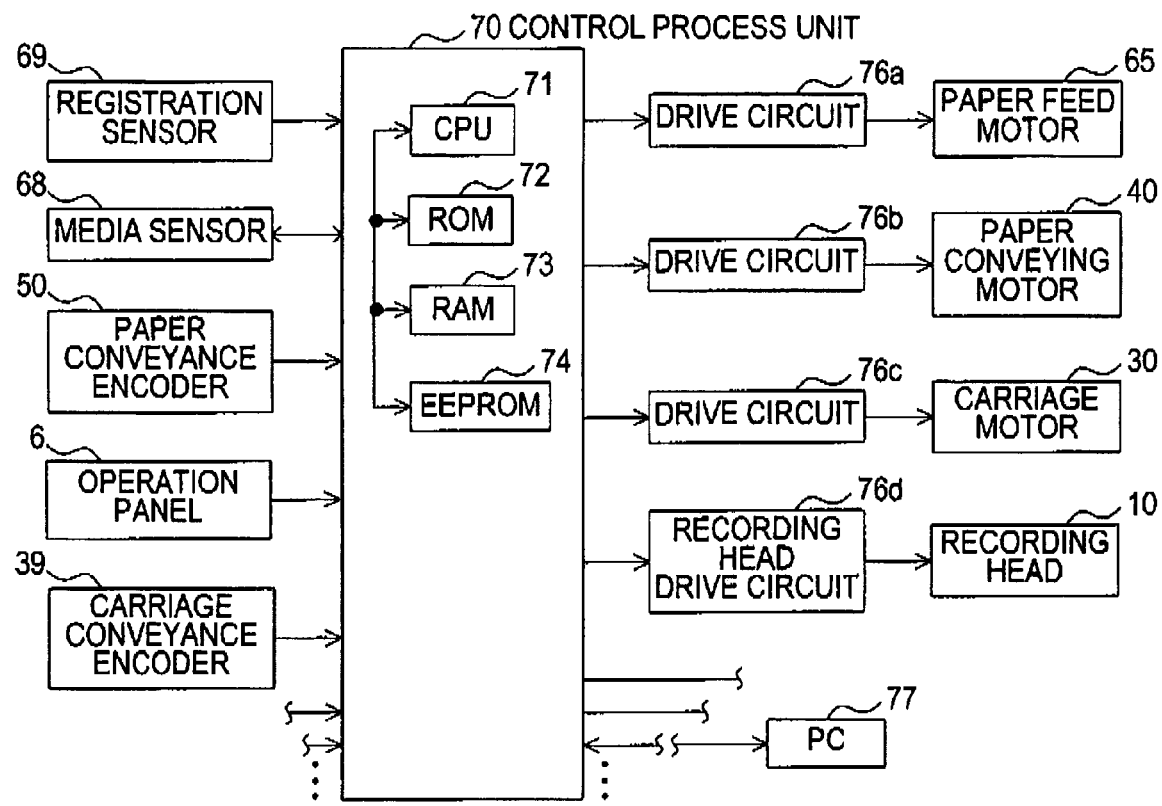
FIG. 4 is a block diagram showing the schematic construction of a control process unit.

A registration sensor 69 is disposed upstream (in the rear side) of the media sensor 68 in the paper conveying direction (see FIG. 4, and not shown in FIG. 2). The registration sensor 69 is a sensor on the upstream side that can detect the existence of paper, as well as the leading edge and trailing edge of paper. Specifically, the registration sensor 69 is attached to the front end of an upper cover that forms the conveying path in the paper supplying unit 2.

The registration sensor 69 may be a mechanical sensor having a probe, a photo interrupter, and a torsion spring. The probe protrudes into a paper-conveying path. When the probe is contacted by the paper which is being conveyed, the probe rotates. The photo interrupter includes a light-emitting unit and a light-receiving unit, and detects the rotation of the probe. The torsion spring urges the probe into the paper-conveying path. A shielding part is integrally provided on the probe. When the probe is rotated by the paper, which is being conveyed, the shielding part becomes positioned outside of the area between the light-emitting unit and the light-receiving unit of the photo interrupter. Hence, light is transmitted from the light-emitting unit to the light-receiving unit, and the registration sensor 69 is in an ON state. However, when the paper is not being conveyed, the probe is urged into the paper-conveying path by the torsion spring. The shielding part becomes positioned between the light-emitting unit and the light-receiving unit. Hence, the transmission of light from the light-emitting unit to the light-receiving unit is interrupted, and the registration sensor 69 is placed in an OFF state.

Next, the configuration of the media sensor 68 will be described.

FIG. 3A is a pattern diagram showing a cross-sectional configuration of the media sensor 68 in a state in which the media sensor 68 is mounted on the recording head 10 (carriage 11). FIG. 3B is an explanatory diagram of a target detection area of the media sensor 68. The media sensor 68 in FIGS. 3A and 3B is seen from the rear side of the printer 3.

As shown in FIGS. 3A and 3B, the media sensor 68 includes a sensor body unit 81 and a cap member 85. The sensor body unit 81 has a light-emitting element 82 and a light-receiving element 83. The cap member 85 is a tubular member having a bottom 85a. The cap member 85 can accommodate the sensor body unit 81 inside the cap member 85.

The end of the light-emitting element 82 in the direction of the central axis thereof (the bottom end in FIGS. 3A and 3B) has a hemispherical configuration. The light-emitting element 82 has an approximately tubular configuration. The external diameter of the light-emitting element 82 is, for example, 2.2 mm. The directivity of the light-emitting element 82 is low (wide angular output range). Further, the light-emitting element 82 is provided with an output unit 82a on the end of the light-emitting element 82. The output unit 82a outputs light for detection. The light for detection is output from the output unit 82a to the paper P.

The end of the light-receiving element 83 in the direction of the central axis thereof (the bottom end in FIGS. 5A and 3B) has a hemispherical configuration. The light-receiving element 83 has an approximately tubular configuration. The external diameter of the light-receiving element 83 is, for example, 2.2 mm. The directivity of the light-receiving element 83 is low (wide angular light-receiving range). Further, the light-receiving element 83 is provided with a light-receiving unit 83a on the end of the light-receiving element 83. The light-receiving unit 83a receives light from the outside. The reflected light of the light for detection, which is reflected from the paper P, is received by the light-receiving unit 83a.

The light-emitting element 82 and the light-receiving element 83 are disposed in the following manner: The direction of the central axis of the light-emitting element 82 is approximately parallel to the direction of the central axis of the light-receiving element 83. The direction of the central axis of each of the light-emitting element 82 and the light-receiving element 83 is the same direction as the vertical direction in relation to the target detection surface of the paper P. The distance between the center position of the output unit 82a and the center position of the light-receiving unit 83a is, for example, set at 2.8 mm. The center position of each of the output unit 82*a* and the light-receiving unit 83*a* is located on an end surface of the sensor body unit 81.

The cap member 85 includes a common opening unit 85*b* at the bottom 85*a*. The common opening unit 85*b* is disposed at a position at which the common opening unit 85*b* passes the light for detection and the reflected light, while controlling so as to reduce the overlapping area on the paper P between the irradiation area of the light for detection and the area from which the light-receiving element 83 can receive light. The common opening unit 85*b* has a circular configuration. The internal diameter of the opening of the common opening unit 85*b* is, for example, 3.0 mm. The thickness of the bottom 85*a* of the cap member 85 is, for example, 1.0 mm. The internal distance between the inner surface of the bottom 85*a* and the end surface of the sensor body unit 81 is, for example, 5.0 mm.

The media sensor 68 is mounted on the sensor mounting unit 10*e* of the recording head 10 so that the external distance between the outer surface of the bottom 85*a* of the cap member 85 and the paper P is, for example, 5.0 mm. The media sensor 68 is disposed so that the center of the opening of the common opening unit 85*b* of the cap member 85 is provided on the line that is extended in the same direction as the vertical direction in relation to the surface of the paper P from the approximately center part of the line that connects the output unit 82*a* of the light-emitting element 82 and the light-receiving unit 83*a* of the light-receiving element 83. The line that connects the output unit 82*a* and the light-receiving unit 83*a* is a line that connects between the center of the output unit 82*a* and the center of the light-receiving unit 83*a*.

Consequently, the area, in which an irradiation area S1*a* of the light for detection by the light-emitting element 82 and a light-receiving area S1*b* by the light-receiving element 83 are overlapped, becomes a target detection area S1 in the media sensor 68 (see FIG. 3B). The irradiation area S1*a* and the light-receiving area S1*b* are both controlled (limited) by the common opening unit 85*b* of the cap member 85.

That is, since the media sensor 68 is configured so that the cap member 85 covers the output unit 82*a* of the light-emitting element 82 and the light-receiving unit 83*a* of the light-receiving element 83, the angular output range of light from the light-emitting element 82 and the angular light-receiving range of light to the light-receiving element 83 are regulated (limited) to be relatively small, and the target detection area S1 is decreased accordingly.

The target detection area of the media sensor 68 is a boarder line between the paper P and the area outside the paper P (i.e. platen 17). As the target detection area S1 of the media sensor 68 is increased, it is easy to be affected by disturbances from the area outside of the target detection area. That is, in the present embodiment the target detection area S1 is decreased as described above so that it is difficult to be affected by disturbances from the area outside of the target detection area.

Next, the control process unit 70 will be described, FIG. 4 is a block diagram showing the schematic construction of the control process unit 70.

As shown in FIG. 4, the control process unit 70 includes a microcomputer having a CPU 71, a ROM 72, a RAM 73, and an EEPROM 74. The control process unit 70 is electrically connected to the registration sensor 69, the media sensor 68, the paper conveyance encoder 50, the operation panel 6, the carriage conveyance encoder 39, and the like.

The control process unit 70 is also electrically connected to drive circuits 76*a* to 76*c*, and a recording head drive circuit 76*d*. The drive circuit 76*a* drives the paper feed motor 65. The drive circuit 76*b* drives the paper conveying motor 40. The drive circuit 76*c* drives the carriage motor 30. The recording head drive circuit 76*d* drives the recording head 10. The control unit 70 is also capable of being connected to a personal computer (PC) 77.

Figure 5:
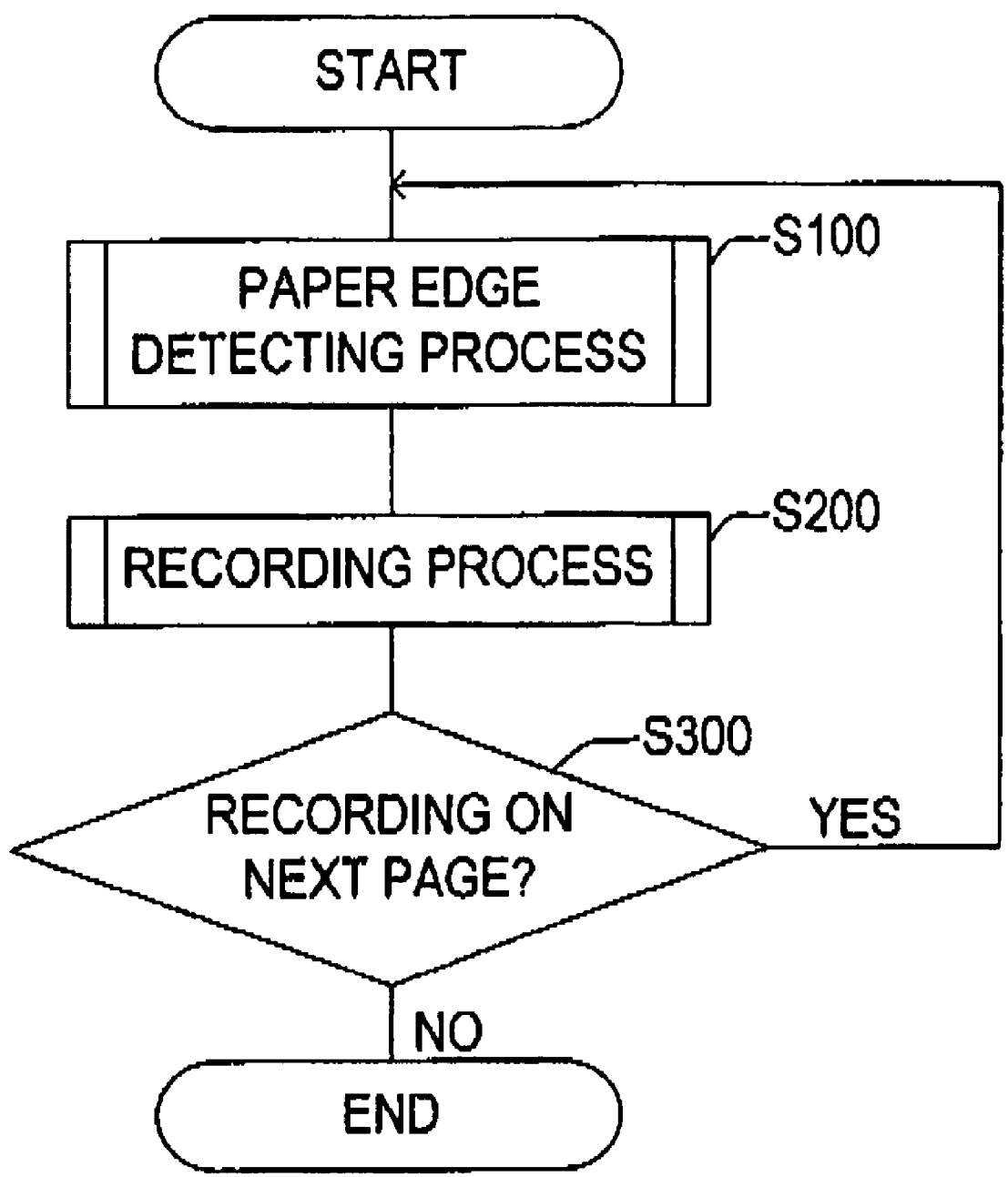
FIG. 5 is a flowchart showing steps executed by the control process device.

When the control process unit 70 (specifically, CPU 71) receives a recording demand to the paper P from the PC 77 or other blocks such as the copier and the facsimile in the multifunction device 1, the control process unit 70 executes an image forming process shown in FIG. 5. As shown in FIG. 5, after performing a paper edge detecting process to detect the edges of the paper P (S100, S indicates a step), the control process unit 70 performs a recording process to form an image on the paper P based on the detection result of the process in S100 (S200). If recording on the next page is required (S300-YES), the paper edge detecting process (S100) and the recording process (S200) are repeatedly performed with respect to the next page of the paper P. If recording on the next page of the paper P is not required (S300-NO), the process shown in FIG. 5 is terminated.

The paper edge detecting process as a main process in the present invention will be described in more detail with reference to the flowchart in FIG. 6.

Figure 6:
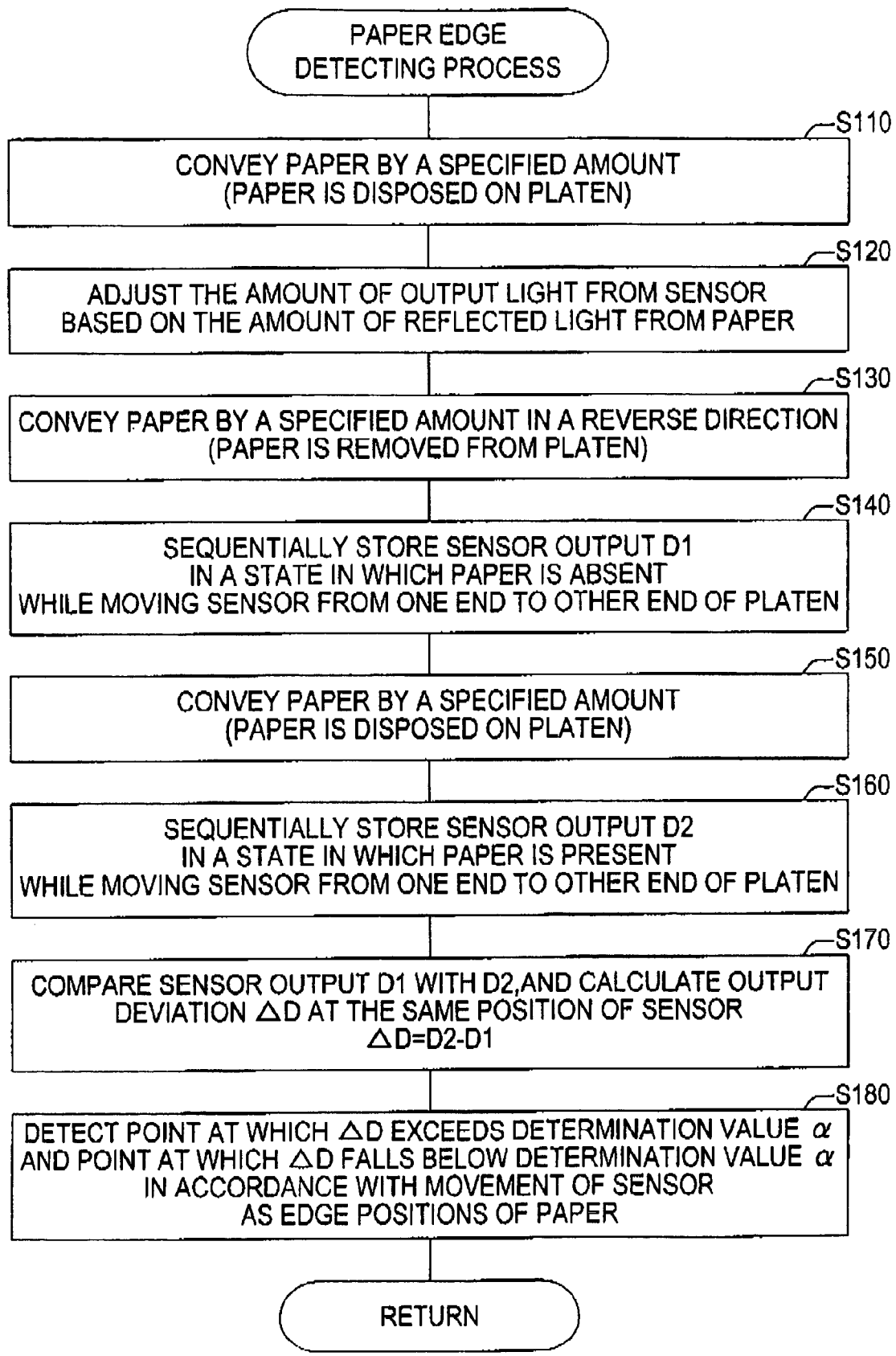
FIG. 6 is a flowchart showing the details of a paper edge detecting process in FIG. 5.

As shown in FIG. 6, in S110 of the paper edge detecting process, the paper feed motor 65 is driven so that the paper P is fed in the printer 3, and the paper conveying motor 40 is driven so that the paper P is further conveyed by a predetermined amount from a position at which the paper edge is detected by the registration sensor 69. Thus, the paper P is disposed on the platen 17.

In S120, the carriage motor 30 is driven so that the media sensor 68 is conveyed along the paper P. The amount of output light from the light-emitting element 82 of the media sensor 68 is adjusted based on a light-receiving signal (the amount of reflected light from the paper P) that is output from the light-receiving element 83 of the media sensor 68 so that the light-receiving signal is at an appropriate level.

In S130, the paper conveying motor 40 is driven in the opposite direction to the paper conveying direction when the paper P is normally conveyed, and the paper P is conveyed by a predetermined amount in the opposite direction. Thus, the paper P is removed from the platen 17. Since the paper P is removed from the platen 17, the light output from the media sensor 68 is not reflected from the paper P. Therefore, only the reflected light from the platen 17 is input to the media sensor 68.

Figure 7A:
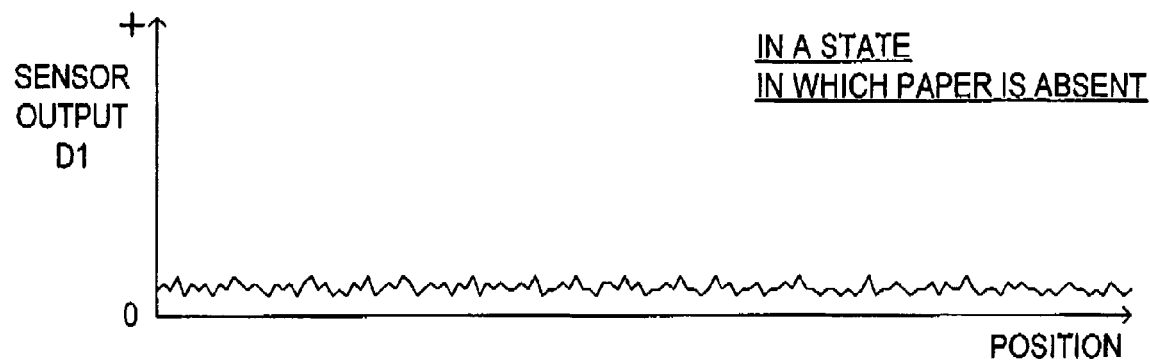
FIGS. 7A, 7B, and 7C are explanatory diagrams showing sensor outputs D1 and D2 sampled and a deviation ΔD therebetween in the paper edge detecting process in FIG. 5.

In S140, the carriage motor 30 is driven so that the media sensor 68 is moved from one end to the other end of the platen 17. The light-receiving signal (i.e., reflected light data) output from the light-receiving element 83 of the media sensor 68 when the media sensor 68 is moved, is sequentially sampled as a sensor output D1 in a state in which paper is absent. The sampled sensor output D1 is associated with the moving position of the carriage 11 (recording head 10) that is detected by the carriage conveyance encoder 39 to be stored in RAM 73. Thus, the chronological data of the sensor output D1 is generated in the state in which paper is absent as shown in FIG. 7A.

After the chronological data of the sensor output D1 is generated in the state in which paper is absent, the process proceeds to S150. The paper conveying motor 40 is driven in the same direction as the direction when an image is formed on the paper, and the paper P is conveyed by a predetermined amount in a forward direction. Thus, the paper P is disposed on the platen 17.

Since the paper P is disposed on the platen 17, the light output from the media sensor 68 is reflected from the paper P and/or the platen 17 in accordance with the position of the media sensor 68. Therefore, the reflected light is inputted from at least one of the platen 17 and the paper P to the media sensor 68 in accordance with the position of the media sensor 68 that intersects with the paper conveying direction.

Figure 7B:
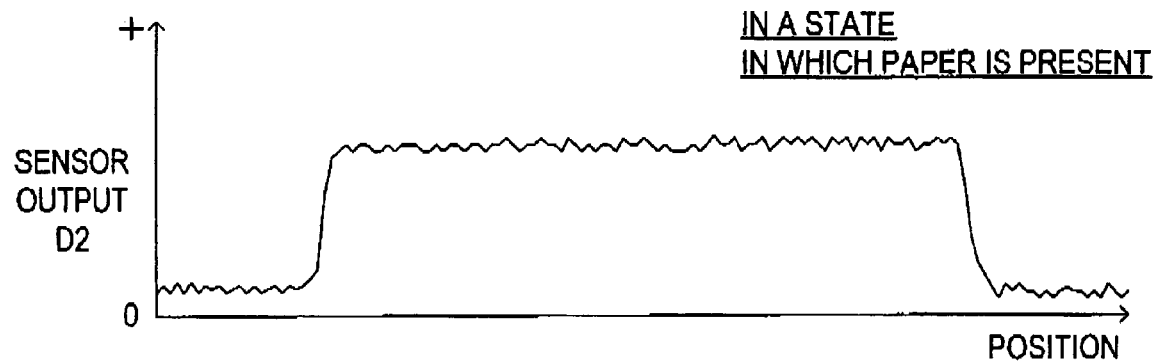

In S160, as in S140, the carriage motor 30 is driven so that the media sensor 68 is moved from one end to the other end of the platen 17. The light-receiving signal (i.e., reflected light data) output from the light-receiving element 83 of the media sensor 68 when the media sensor 68 is moved is sequentially sampled as a sensor output D2 in a state in which paper is present the sampled sensor output D2 is associated with the moving position of the carriage 11 (recording head 10) that is detected by the carriage conveyance encoder 39 to be stored in RAM 73. Thus, the chronological data of the sensor output D2 is generated in the state in which paper is present as shown in FIG. 7B.

In S170, the chronological data of the sensor output D1, which has been generated in S140, is compared to the chronological data of the sensor output D2, which has been generated in S160. The deviation values $\Delta D$ ($\Delta D = D2 - D1$) between the sensor outputs D1 and D2, which have been sampled when the carriage 11 (recording head 10) is located at the same position with respect to the platen 17, are sequentially calculated. Thus, the chronological data of the deviation value $\Delta D$ is generated as shown in FIG. 7C.

Figure 7C:
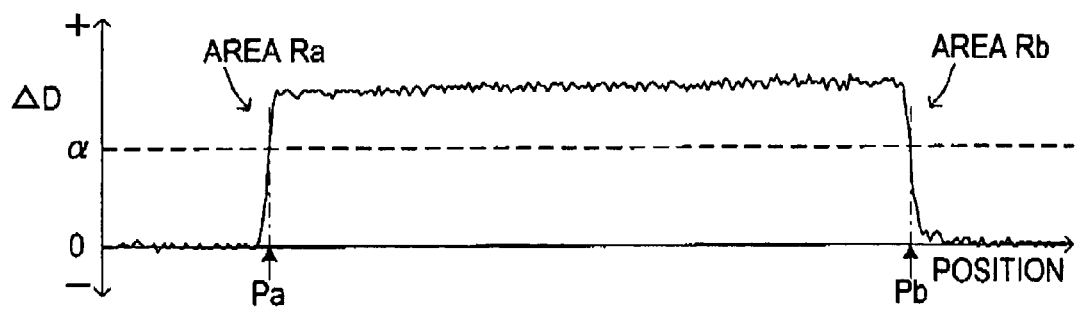

In S180, as shown in FIG. 7C, each of an area Ra and an area Rb is selected as an area in the vicinity of the edge of the paper P based on the chronological data of the deviation value $\Delta D$ generated in S170. The area Ra is selected as an area where the deviation value $\Delta D$ tends to be increased. The area Rb is selected as an area where the deviation value $\Delta D$ tends to be decreased, Then each of a point Pa and a point Pb is detected as an edge position of the paper P. The point Pa is detected as a point at which the deviation value $\Delta D$ exceeds a predetermined determination value $\alpha$ in the area Ra, in which the deviation value $\Delta D$ tends to be increased. The point Pb is detected as a point at which the deviation value $\Delta D$ falls below the predetermined determination value $\alpha$ in the area Rb, in which the deviation value $\Delta D$ tends to be decreased. The moving position of the carriage 11 (recording head 10) at each of the points Pa, Pb is stored as the edge position of the paper P in RAM 73. Then, the paper edge detecting process is terminated, In S180, if there are a plurality of points Pa, at which the deviation value $\Delta D$ exceeds the predetermined determination value $\alpha$ in the area in which the deviation value $\Delta D$ tends to be increased, or if there are a plurality of points Pb, at which the deviation value $\Delta D$ falls below the determination value $\alpha$ in the area in which the deviation value $\Delta D$ tends to be decreased, the innermost point among the plurality of points on the paper P is selected as the edge position of the paper P.

Even in the area in the vicinity of the edge position of the paper P that has been selected as the area in which the deviation value $\Delta D$ tends to be increased or decreased, the deviation value $\Delta D$ may temporarily exceed the determination value $\alpha$ due to noise during the sampling of the sensor outputs D1 and D2. By selecting the innermost point as above, the edge positions of the paper P can be more precisely detected without being influenced by the noise.

As described above, according to the multifunction device 1 in the present embodiment, when the image is formed on the paper P by the printer 8 as the image forming device, the edge position in the width direction of the paper P is detected using the media sensor 68 mounted on the carriage 11 (recording head 10). The edge position is detected in the following manner. First, the carriage 11 is respectively moved from one end to the other end of the platen 17 when the paper P is and is not disposed on the platen 17 as a supporting member to support the paper P as the target detection object. When the carriage 11 is moved, the output from the media sensor 68 is sampled. The chronological data (second reflected light data: see FIG. 7A) of the sensor output D1 is generated in the state in which paper is absent. The chronological data (first reflected light data: see FIG. 7B) of the sensor output D2 is generated in the state in which paper is present. The chronological data of the sensor output D2 is compared with the chronological data of the sensor output D1. The relative change point (see points Pa and Pb in FIG. 7C) of each chronological data is detected based on the deviation $\Delta D$ between the sensor output D2 and the sensor output D1.

Therefore, according to the multifunction device 1 in the present embodiment, when the image is formed on the paper P by the printer 3, both side edge positions of the paper P can be accurately detected without being affected by irregularity in color, concavity and convexity on the surface of the paper P and by the curl-up/down of the edge positions of the paper P. Then, the image forming operation is started. Thus, the image can be preferably formed on the paper P.

According to the conventional paper edge detecting method as seen in FIG. 8, the paper P on the platen 17 is optically scanned by the media sensor 68. The chronological data of the light-receiving signal that is output from the media sensor 68 when the paper P is scanned, is split between a solid black area constituted only by the reflected light from the platen 17 and a solid white area constituted only by the reflected light from the paper P. The middle point interposed between the solid black area and the solid white area is detected as the edge of the paper P (paper edge). In the conventional paper edge detecting method as above, if the color on the surface of the paper P is approximately constant, the paper P is smooth, and the paper P is pressed onto the platen 17, then, the paper edge can be accurately detected.

However, according to the conventional paper edge detecting method, if the color on the surface of the paper P is not constant due to a stain or the like, the paper P is not smooth, or the edge of the paper P is curled up/down with respect to the platen 17, the solid white area can not be accurately distinguished from the chronological data of the sensor output, as shown in the graphs with broken lines. Thus, the edge positions of the paper P are erroneously detected.

According to the present embodiment, the change point of the chronological data (first reflected light data) of the sensor output D2 in the state in which paper is present, is detected based on the chronological data (second reflected light data) of the sensor output D1 in the state in which paper is absent. The change point is specified as the edge position of the paper P. Thus, both edge positions of the paper P can be accurately detected without being affected by irregularity in color, concavity and convexity of the paper P, and by the curl up/down of the paper edge. In the printer 3, the image can be accurately formed on the entire area of the paper P.

Furthermore, according to the present embodiment, in S120, the amount of output light from the light-emitting element 82 of the media sensor 68 is adjusted so that the light-receiving signal from the light-receiving element 83 is at an appropriate level when the reflected light from the paper P is input to the light-receiving element 83. This adjustment is performed before the process of S160 in which the chronological data (first reflected light data) of the sensor output D2 is generated in the state in which paper is present.

This prevents occurrence of following problems, when in S160, the chronological data (first reflected light data) of the sensor output D2 is generated in the state in which paper is present. That is, it is prevented that the amount of input light to the light-receiving element 83 of the media sensor 68 is so increased that the light-receiving signal is saturated. Alternatively, it is prevented that the amount of input light to the light receiving element 83 of the media sensor 68 is so decreased that the detection accuracy of the paper edge is decreased.

While the invention has been described in detail with reference to the specific embodiments thereof, it would be apparent to those skilled in the art that various changes and modifications may be made therein N without departing from the spirit of the invention.

In the present embodiment, the paper edge detecting process is performed in the following manner. First, the paper P is disposed on the platen 17 (S110). After the amount of output light from the light-emitting element 82 of the media sensor 68 is adjusted (S120), the paper P is removed from the platen 17 (S130). The chronological data (second reflected light data) of the sensor output D1 is generated in the state in which paper is absent (S140). Thereafter, the paper P is conveyed onto the platen 17 (S150). The chronological data (first reflected light data) of the sensor output D2 is generated in the state in which paper is present (S160). In this case, the paper P must be conveyed at least three times in forward, reverse, and forward directions for paper edge detection. If the target detection area S1 of the media sensor 68 is located more downstream in the conveying direction of the paper P than an ejection area of ink output from the recording head 10, the paper P needs to be further conveyed in the reverse direction before the process proceeds to the recording process (S200) in FIG. 5.

Figure 9:
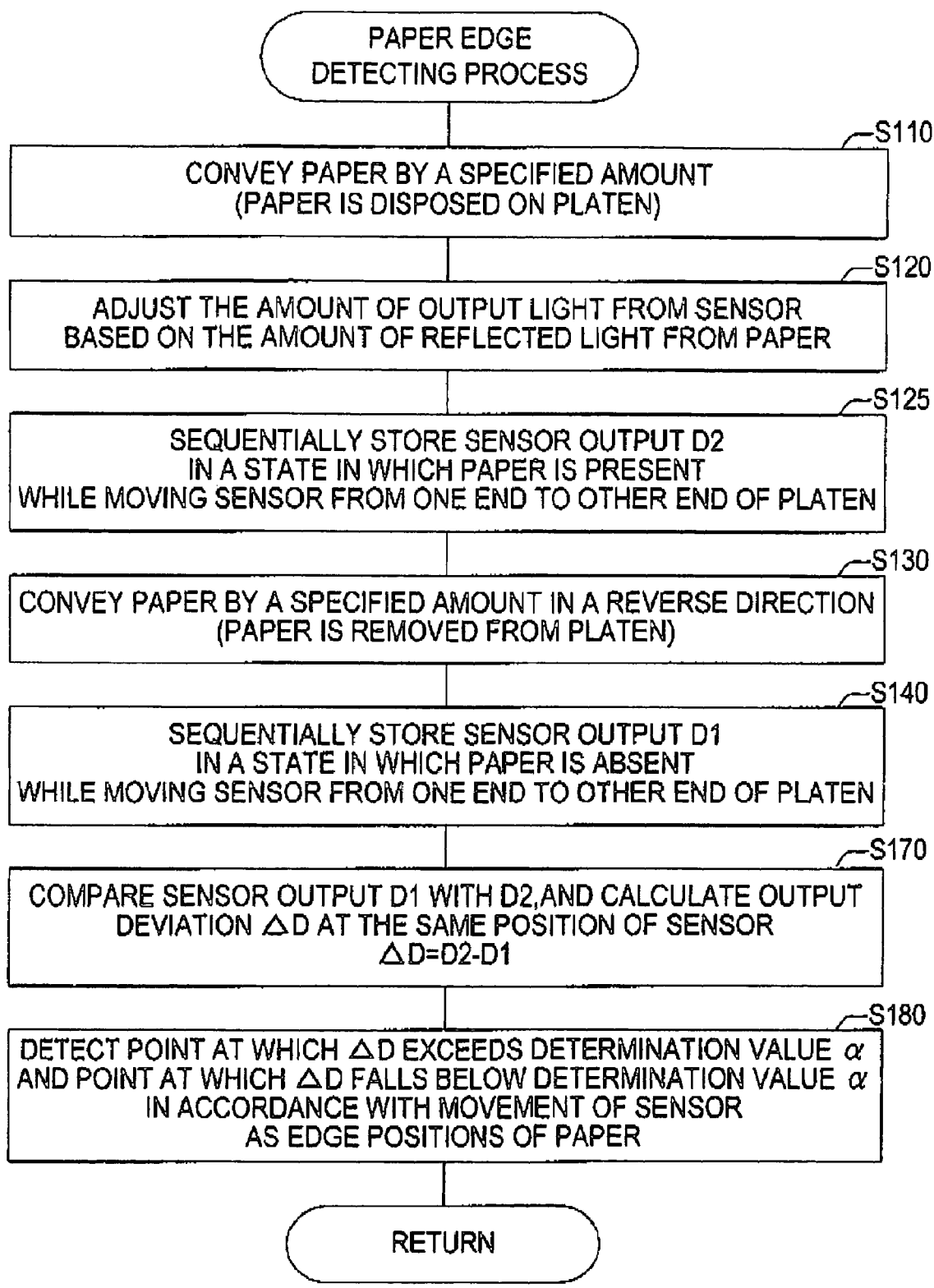
FIG. 9 is a flowchart showing another example of the paper edge detecting process.

In order to reduce the number of conveyances of the paper P in the paper edge detecting process, as shown in FIG. 9, the paper edge detecting process may be performed in the following manner. First, the paper P is disposed on the platen 17 (S110). The amount of output light from the light-emitting element 82 of the media sensor 68 is adjusted (S120). The chronological data (first reflected light data) of the sensor output D2 is generated in the state in which paper is present S125). The paper P is removed from the platen 17 (S130). The chronological data (second reflected light data) of the sensor output D1 is generated in the state in which paper is absent (S140). Thereafter, the process proceeds to S170.

In this case, after the paper P is once conveyed onto the platen 17, the paper P is conveyed only in the reverse direction for paper edge detection. This reduces the number of conveyance of paper in the paper edge detecting process. Further, even if the target detection area S1 of the media sensor 68 is located more downstream in the conveying direction of the paper P than the ejection area of ink output from the recording head 10, the paper P is returned to a position where the paper P is removed from the platen 17 when the paper edge detecting process ends. Therefore, the paper P does not need to be conveyed in the reverse direction before the process proceeds to the recording process (S200) in FIG. 5.

In the paper edge detecting processes shown in FIGS. 6 and 9, the paper P that is once conveyed onto the platen 17 needs to be removed from the platen 17. Therefore, these processes are applicable to the printer 3 in which the paper conveying motor 40 can be reversely rotated and the paper P can be conveyed in the reverse direction. However, these processes are not applicable to a printer in which the paper can not be conveyed in the reverse direction.

Figure 10:
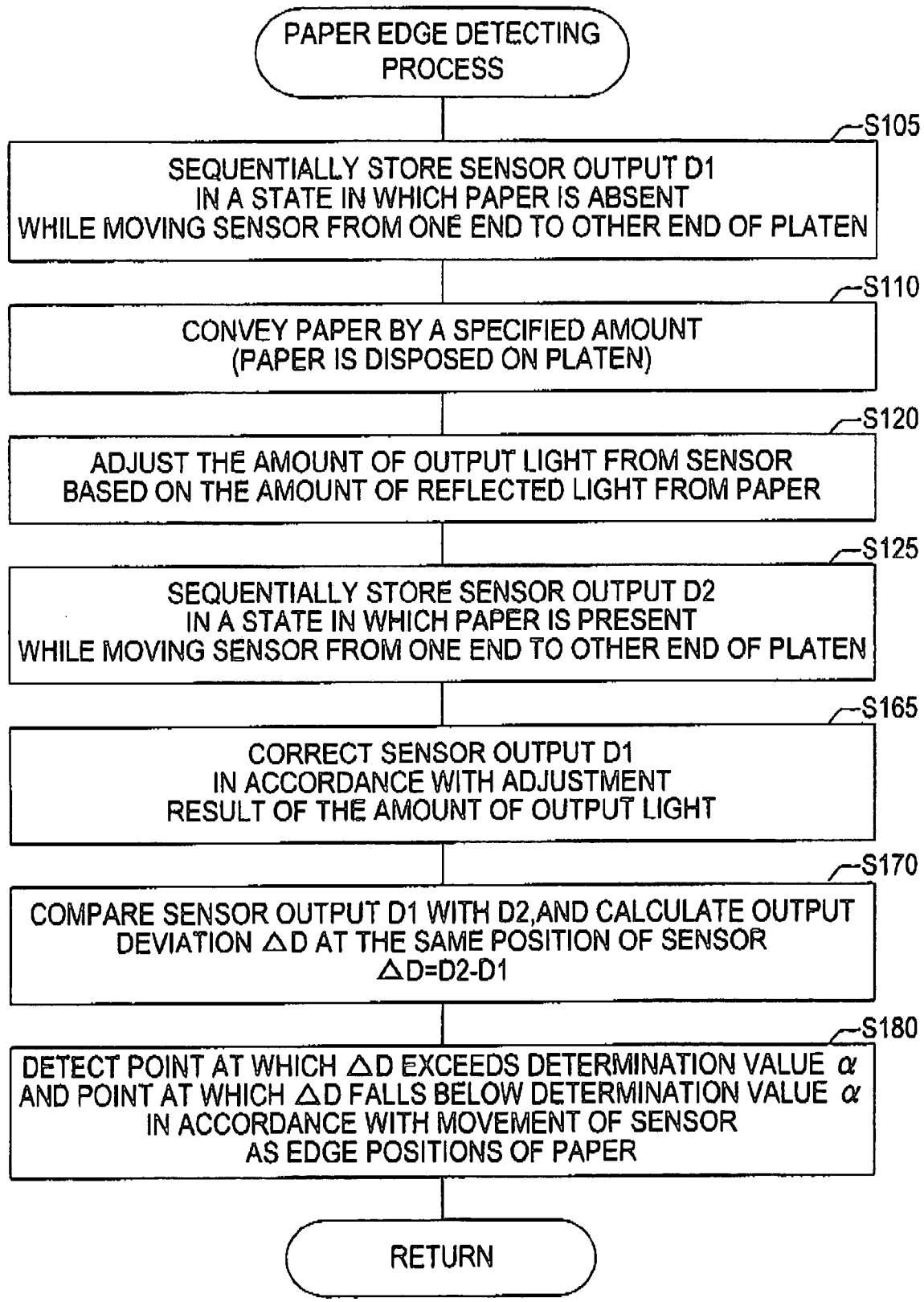
FIG. 10 is a flowchart showing an example of the paper edge detecting process in which the paper edge detection is performed without conveying paper in opposing directions.

In order to apply the present invention to a printer in which the paper P can not be conveyed in the opposite direction to the paper conveying direction when the image is normally formed, the paper edge detecting process may be performed according to the procedure shown in FIG. 10 or 11.

The paper edge detecting process shown in FIG. 10 is performed in the following manner. First, the carriage motor 30 is driven to move the media sensor 68 from one end to the other end of the platen 17 before the paper P is conveyed (i.e. in the state in which paper is not disposed on the platen 17) (S105). Accordingly, the chronological data (second reflected light data) of the sensor output D1 is generated in the state in which paper is absent (S105). Then, the paper feed motor 65 is driven to dispose the paper P on the platen 17 (S110). The amount of output light from the light-emitting element 82 of the media sensor 68 is adjusted (S120). The chronological data (first reflected light data) of the sensor output D2 is generated in the state in which paper is present (S125).

Thereafter, in S165, the chronological data (second reflected light data) of the sensor output D1 in the state in which paper is absent, is corrected in accordance with the adjustment result of the amount of output light in S120. This correction is made so that the data value of the sensor output D1 obtained before the adjustment of the amount of output light from the media sensor 68, and the data value that is obtained based on the reflected light from the surface of the platen 17 among the data values of the sensor output D2 obtained after the adjustment, are approximately the same. Then the process proceeds to S170.

On the other hand, the paper edge detecting process shown in FIG. 11 is performed in the following manner. First, in S102, an initial value "1" is set to a counter "n". In S105, the carriage motor 30 is driven to move the media sensor 68 from one end to the other end of the platen 17, and the chronological data of the sensor output D1n is generated in the state in which paper is absent. Then in S106, it is determined whether the value of the counter "n" is equal to or more than a predetermined value "nx". If n<nx, the amount of output light from the light emitting element 82 of the media sensor 68 is changed (S107). Then, after the counter "n" is incremented (S108), the process again proceeds to S105. Therefore, the chronological data (second reflected light data) of the sensor output D1n is generated a plurality (nx) of times in the state in which paper is absent, while the amount of output light from the light-emitting element 82 of the media sensor 68 is changed.

Thereafter, the paper feed motor 65 is driven in order to dispose the paper P on the platen 17 (S110). The amount of output light from the light-emitting element 82 of the media sensor 68 is corrected (S120). The chronological data (first reflected light data) of the sensor output D2 is generated in the state in which paper is present (S125). Then in S167, the chronological data (second reflected light data) of the sensor output D1, that is measured at the amount of output light closest to the amount of the output light after the adjustment in S120, is selected as the chronological data (second reflected light data) of the sensor output D1 for edge position detection among the plurality of pieces of chronological data (second reflected light data) measured in S105 in the state in which paper is absent. Then the process proceeds to S170.

Therefore, according to the paper edge detecting process as shown in FIG. 10 or 11, the following process needs to be performed. That is, the chronological data (second reflected light data) of the sensor output D1 generated in the state in which paper is absent needs to be corrected based on the adjustment result of the amount of output light from the media sensor 68. Alternatively, the chronological data (second reflected light data) of the sensor output D1 generated in the state in which paper is absent, needs to be generated a plurality of times, while the amount of output light from the media sensor 68 is changed. However, the paper P does not need to be conveyed in the reverse direction for the paper edge detection. Therefore, even a printer that is incapable of conveying the paper P in the reverse direction can perform the paper edge detection in accordance with the method of the present invention. The application range of the present invention can be increased.

In the paper edge detecting process in FIG. 10, when the chronological data (second reflected light data) of the sensor output D1 in the state in which paper is absent is corrected, the sensor output D1 may be corrected based on the ratio B/A so that D1←D1×B/A. Here the value "A" is the value of the drive current supplied to the light-emitting element 82 of the media sensor 68 when the chronological data (second reflected light data) of the sensor output D1 is generated. The value "B" is the value of the drive current supplied to the light-omitting element 82 after the adjustment of the amount of output light from the light-emitting element 82. Here "after the adjustment" is when the chronological data of the sensor output D2 is generated in the state in which paper is present.

In the above, the value "A" may be the value of drive duty of the light-emitting element 82 when the chronological data (second reflected light data) of the sensor output D1 is generated. The value "B" may be the value of drive duty of the light-emitting element 82 when the chronological data (first reflected light data) of the sensor output D2 is generated.

According to the paper edge detecting process in FIG. 11, a plurality of pieces of chronological data (second reflected light data) of the sensor output D1 are generated in the state in which paper is absent. Then the chronological data (second reflected light data) that is measured at the amount of output light closest to the amount of output light after the adjustment in S120 is selected from the plurality of pieces of chronological data (second reflected light data).

In this case, the drive current (or drive duty) that is the closest to the drive current (or drive duty) of the light-emitting element 82 after the adjustment of the amount of output light from the light-emitting element 82 may be selected from each of the drive current (or drive duty) of the light-emitting element 82 when the plurality of pieces of the chronological data (second reflected light data) are generated. In this case, the chronological data (second reflected light data) corresponding to the selected drive current (or selected drive duty) may be selected for paper edge detection.

Instead of the above selecting, two pieces of chronological data (second reflected light data) may be selected. In this case, one chronological data DA out of the selected two pieces of chronological data (second reflected light data) is the data measured at the amount of output light that is the closest to the amount of output light after the adjustment in S120 within one or more pieces of the chronological data (second reflected light data) measured at the amount of output light that exceeds the amount of output light after the adjustment in S120. The other chronological data DB is the data measured at the amount of output light that is the closest to the amount of output light after the adjustment in S120 within one or more pieces of the chronological data (second reflected light data) measured at the amount of output light that is below the amount of output light after the adjustment in S120.

In this case, the sensor output D1 in the state in which paper is absent for paper edge detection may be calculated using the following equation based on CA, CB, and CC in addition to the two pieces of selected chronological data DA and DB.

$$D1=(DA+DB)\times\{(CC-CA)/(CB-CA)\}$$

In the above equation, each of the CA and CB is the drive current (or drive duty) of the light-emitting element 82 when each of the chronological data DA and DB is generated. The CC is the drive current (or drive duty) of the light-emitting element 82 after the adjustment (S120) of the amount of output light from the light-emitting element 82.

When the chronological data (second reflected light data) of the sensor output D1 in the state in which paper is absent is corrected, the drive current supplied to the light-emitting element 82, or the drive duty of the light-emitting element 82 after the adjustment of the amount of output light, is not necessarily used. The sensor output DD2 that is obtained by receipt of the reflected light from the platen 17 may be extracted from the chronological data (first reflected light data) of the sensor output D2 in the state in which paper is present. In this case, the average value of the difference between the sensor output DD2 and the sensor output D1 at the corresponding position is determined as the correction value. The chronological data (second reflected light data) of the sensor output D1 in the state in which paper is absent, is corrected using the correction value.

According to the above embodiment, as described above, the edge positions of the paper P are detected in the following manner: The sensor outputs D1 and D2, that are sampled at the same position in relation to the platen 17, are sequentially extracted from the chronological data (second reflected light data) generated in the state in which paper is absent and the chronological data (first reflected light data) generated in the state in which paper is present. The deviation value ΔD is determined based on the extracted sensor outputs D1 and D2. The point at which the deviation value ΔD exceeds the determination value α and the point at which the deviation value ΔD falls below the determination value α are detected as the edge positions (both edges) of the paper P. However, for example, the square value of the deviation value ΔD calculated as above may be determined. In this case, the point at which the square value exceeds a threshold value for edge position determination and the point at which the square value falls below the threshold value may be detected as the edge positions (both edges) of the paper P. This will increase the detection sensitivity of the relative changing point (edge position) of the first reflected light data with respect to the second reflected light data.

The square root of the deviation value ΔD calculated as above may be determined. The point at which the square root exceeds a threshold value for edge position determination and the point at which the square root falls below the threshold value may be detected as the edge positions (both edges) of the paper P. This will decrease the detection sensitivity of the relative changing point (edge position) of the first reflected light data with respect to the second reflected light data.

In the above embodiment, the color of the platen 17 is described as black. However the color of the platen 17 may be any color, as long as the color of the surface of the platen 17 absorbs light more easily than the color of the surface of the paper as a target detection object or a recording medium.

What is claimed is:

1. An edge position detecting apparatus, comprising:
a reflective optical sensor that outputs light to a supporting surface of a supporting member to support a target detection object, and that receives a reflected light;
a moving unit that moves the reflective optical sensor along the supporting surface of the supporting member in a specified direction;
a reflected light data generating unit that generates a reflected light data when one of the supporting member and the target detection object on the supporting member is optically scanned in the specified direction by obtaining a light-receiving signal from the reflective optical sensor while moving the reflective optical sensor via the moving unit in the specified direction; and
a detecting unit that detects an edge position of the target detection object in the specified direction based on the reflected light data generated by the reflected light data generating unit,
wherein the reflected light data generating unit generates the reflected light data respectively when the target detection object is supported by the supporting member and when the target detection object is not supported by the supporting member,
wherein the detecting unit detects the edge position based on a relative change between a first reflected light data and a second reflected light data, where the first reflected light data is generated by the reflected light data generating unit when the target detection object is supported by the supporting member, and the second reflected light data is generated by the reflected light data generating unit when the target detection object is not supported by the supporting member,
wherein the detecting unit determines a deviation between a data value of the first reflected light data and a data value of the second reflected light data at each detection position that changes in accordance with movement of the reflective optical sensor,
and wherein the detecting unit detects one of a position at which a data value related to the deviation exceeds a predetermined threshold value and a position at which the data value related to the deviation falls below a predetermined threshold value as an edge position of the target detection object.

2. The edge position detecting apparatus according to claim 1,
wherein the data value is equal to the deviation.

3. The edge position detecting apparatus according to claim 1,
wherein the data value is a square value of the deviation.

4. The edge position detecting apparatus according to claim 1,
wherein the data value is a square root of the deviation.

5. The edge position detecting apparatus according to claim 2, wherein when the detecting unit detects a plurality of edge positions in one of an area in which the deviation between the data value of the first reflected light data and the data value of the second reflected light data tends to be increased in accordance with the movement of the reflective optical sensor and an area in which the deviation tends to be decreased in accordance with the movement of the reflective optical sensor, the detecting unit selects an edge position that is located innermost in the target detection object among the plurality of detected edge positions, and the detecting unit specifies a selected edge position as an edge position of the target detection object.

6. The edge position detecting apparatus according to claim 1, wherein a color of the supporting surface of the supporting member absorbs light more easily at least than a color of a surface of the target detection object, and
the reflected light data generating unit adjusts an amount of output light from the reflective optical sensor when generating the first reflected light data so that a light-receiving signal when the reflective optical sensor receives a reflected light from the target detection object is at an adequate level, and subsequently staffs generating the reflected light data.

7. The edge position detecting apparatus according to claim 1, wherein the supporting member conveyably supports a recording medium on which an image is formed in an image forming apparatus,
the reflective optical sensor is disposed so that the reflective optical sensor is capable of being moved along the supporting surface of the supporting member in a width direction perpendicular to a conveying direction of the recording medium, and
the detecting unit detects the edge position of the recording medium in the width direction based on the first and second reflected light data obtained from the reflected light data generating unit.

8. An edge position detecting apparatus comprising:
a reflective optical sensor that outputs light to a supporting surface of a supporting member to support a target detection object, and that receives a reflected light;
a moving unit that moves the reflective optical sensor along the supporting surface of the supporting member in a specified direction;
a reflected light data generating unit that generates a reflected light data when one of the supporting member and the target detection object on the supporting member is optically scanned in the specified direction by obtaining a light-receiving signal from the reflective optical sensor while moving the reflective optical sensor via the moving unit in the specified direction; and
a detecting unit that detects an edge position of the target detection object in the specified direction based on the reflected light data generated by the reflected light data generating unit,
wherein the reflected light data generating unit generates the reflected light data respectively when the target detection object is supported by the supporting member and when the target detection object is not supported by the supporting member,
wherein the detecting unit detects the edge position based on a relative change between a first reflected light data and a second reflected light data, where the first reflected light data is generated by the reflected light data generating unit when the target detection object is supported by the supporting member, and the second reflected light data is generated by the reflected light data generating unit when the target detection object is not supported by the supporting member,
wherein the reflected light data generating unit generates the first reflected light data after generating the second reflected light data,
wherein the detecting unit corrects the second reflected light data based on an adjustment result of the amount of output light by the reflected light data generating unit so that a data value obtained based on the reflected light from the supporting surface of the supporting member among data values in the first reflected light data and a data value in the second reflected light data are approximately the same,
and wherein the detecting unit detects the edge position based on a corrected second reflected light data and the first reflected light data.

9. An edge position detecting apparatus comprising:
a reflective optical sensor that outputs light to a supporting surface of a supporting member to support a target detection object, and that receives a reflected light;
a moving unit that moves the reflective optical sensor along the supporting surface of the supporting member in a specified direction;
a reflected light data generating unit that generates a reflected light data when one of the supporting member and the target detection object on the supporting member is optically scanned in the specified direction by obtaining a light-receiving signal from the reflective optical sensor while moving the reflective optical sensor via the moving unit in the specified direction; and
a detecting that detects an edge position of the target detection object in the specified direction based on the reflected light data generated by the reflected light data generating unit,
wherein the reflected light data generating unit generates the reflected light data respectively when the target detection object is supported by the supporting member and when the target detection object is not supported by the supporting member,
wherein the detecting unit detects the edge position based on a relative change between a first reflected light data and a second reflected light data, where the first reflected light data is generated by the reflected light data generating unit when the target detection object is supported by the supporting member, and the second reflected light data is generated by the reflected light data generating unit when the target detection object is not supported by the supporting member,
wherein the reflected light data generating unit generates the first reflected light data after generating a plurality of pieces of the second reflected light data by changing the amount of output light from the reflective optical sensor in a stepwise manner,
wherein the detecting unit selects a second reflected light data from the plurality of the second reflected light data, where a selected second reflected light data includes a data value that is the closest to a data value obtained based on a reflected light from the supporting surface of the supporting member among data values in the first reflected light data, and
wherein the detecting unit detects the edge position based on the selected second reflected light data and the first reflected light data.

10. An edge position detecting method, comprising steps of:
outputting light to a supporting surface of a supporting member to support a target detection object and receiving a reflected light via a reflective optical sensor,
obtaining a light-receiving signal from the reflective optical sensor while moving the reflective optical sensor along the supporting surface of the supporting member in a specified direction,
generating a reflected light data when one of the supporting member and the target detection object on the supporting member is optically scanned in the specified direction, and
detecting an edge position of the target detection object in the specified direction based on the generated reflected light data such that the edge position,
wherein the reflected light data is respectively generated when the target detection object is supported by the supporting member and when the target detection object is not supported by the supporting member,
wherein the edge position of the target detection object is detected based on a relative change between a first reflected light data and a second reflected light data, where the first reflected light is generated by the reflected light data generating unit when the target detection object is supported by the supporting member, and the second reflected light data is generated by the reflected light data generating unit when the target detection object is not supported by the supporting member,
wherein a deviation between a data value of the first reflected light data and a data value of the second reflected light data is determined at each detection position that change in accordance with movement of the reflective optical sensor, and
wherein one of a position at which a data value related to the deviation exceeds a predetermined threshold value and a position at which the data value related to the deviation falls below a predetermined threshold value is detected as the edge position of the target detection object.

11. The edge position detecting method according to claim 10,
wherein the data value related to the deviation is the deviation.

12. The edge position detecting method according to claim 10,
wherein the data value related to the deviation is a square value of the deviation.

13. The edge position detecting method according to claim 10,
wherein the data value related to the deviation is a square root of the deviation.

14. The edge position detecting method according to claim 11, wherein when a plurality of edge positions in one of an area in which the deviation between the data value of the first reflected light data and the data value of the second reflected light data tends to be increased in accordance with the movement of the reflective optical sensor and an area in which the deviation between the data value of the first reflected light data and the data value of the second reflected light data tends to be decreased in accordance with the movement of the reflective optical sensor are detected, an edge position that is located innermost in the target detection object among the plurality of detected edge positions is selected,
and a selected edge position is specified as the edge position of the target detection object.

15. The edge position detecting method according to claim 10, wherein a color of the supporting surface of the supporting member absorbs light more easily at least than a color of a surface of the target detection object, and
when the first reflected light data is generated, an amount of output light from the reflective optical sensor is adjusted so that a light-receiving signal generated when the reflective optical sensor receives a reflected light from the target detection object is at an adequate level,
and subsequently the light-receiving signal is obtained from the reflective optical sensor while the reflective optical sensor is moved along the supporting surface of the supporting member in the specified direction, and thus the first reflected light data is generated.

16. An edge position detecting method comprising:

outputting light to a supporting surface of a supporting member to support a target detection object and receiving a reflected light via a reflective optical sensor, obtaining a light-receiving signal from the reflective optical sensor while moving the reflective optical sensor along the supporting surface of the supporting member in a specified direction, generating a reflected light data when one of the supporting member and the target detection object on the supporting member is optically scanned in the specified direction, and detecting an edge position of the target detection object in the specified direction based on the generated reflected light data as based on a relative change between a first reflected light data and a second reflected data, where the first reflected light is generated by reflected light data generating unit when the target detection object is supported by the supporting member, and the second reflected light data is generated by the reflected light data generating unit when the target detection object is not supported by the supporting member, wherein the reflected light data is respectively generated when the target detection object is supported by the supporting member and when the target detection object is not supported by the supporting member, wherein the first reflected light data is generated after the second reflected light data is generated, when the edge position of the target detection object is detected using the generated reflected light data, the second reflected light data is corrected based on an adjustment result of the amount of output light adjusted when the first reflected light data is generated so that a data value obtained based on the reflected light from the supporting surface of the supporting member among data values in the first reflected light data and a data value in the second reflected light data are approximately the same, and wherein the edge position is detected based on a corrected second reflected light data and the first reflected light data.

17. An edge position detecting method comprising:

outputting light to a supporting surface of a supporting member to support a target detection object and receiving a reflected light via a reflective optical sensor, obtaining a light-receiving signal from the reflective optical sensor while moving the reflective optical sensor along the supporting surface of the supporting member in a specified direction, generating a reflected light data when one of the supporting member and the target detection object on the supporting member is optically scanned in the specified direction, and detecting an edge position of the target detection object in the specified direction based on the generated reflected light data as based on a relative change between a first reflected light data and a second reflected light data, where the first reflected light is generated by reflected light data generating unit when the target detection object is supported by the supporting member, and the second reflected light data is generated by the reflected light data generating unit when the target detection object is not supported by the supporting member, wherein the reflected light data is respectively generated when the target detection object is supported by the supporting member and when the target detection object is not supported by the supporting member, wherein the first reflected light data is generated after the second reflected light data is generated, wherein, when the second reflected light data is generated, a plurality of pieces of the second reflected light data are generated by changing the amount of output light from the reflective optical sensor in a stepwise manner, wherein, when the edge position of the target detection object is detected using the generated reflected light data, a second reflected light data is selected from the plurality of pieces of the second reflected light data, where a selected second reflective light data includes data value that is the closest to a data value obtained based on the reflected light from the supporting surface of the supporting member among data values in the first reflected light data, and wherein the edge position is detected based on the selected second reflected light data and the first reflected light data.

18. A computer readable storage medium having computer-executable instructions stored thereon for use in an edge position detecting system including a reflective optical sensor that outputs light to a supporting surface of a supporting member to support a target detection object, and that receives reflected light, and a moving unit that moves the reflective optical sensor along the supporting surface of the supporting member in a specified direction, wherein the instructions when executed by a computer perform a method comprising the steps of;

generating reflected light data when one of the supporting member and the target detection object on the supporting member is optically scanned in the specified direction, and detecting an edge position of the target detection object in the specified direction based on the generated reflected light data, wherein the reflected light data is respectively generated when the target detection object is supported by the supporting member and when the target detection object is not supported by the supporting member, wherein the edge position of the target detection object is detected based on a relative change between a first reflected light data and a second reflected light data, where the first reflected light is generated by the reflected light data generating unit when the target detection object is supported by the supporting member, and the second reflected light data is generated by the reflected light data generating unit when the target detection object is not supported by the supporting member wherein the detecting unit determines a deviation between a data value of the first reflected light data and a data value of the second reflected light data at each detection position that changes in accordance with movement of the reflective optical sensor, and wherein the detecting unit detects one of a position at which a data value related to the deviation exceeds a predetermined threshold value and a position at which the data value related to the deviation falls below a predetermined threshold value as an edge position of the target detection object.

* * * * *